(12) United States Patent
Onuma

(10) Patent No.: US 8,580,198 B2
(45) Date of Patent: Nov. 12, 2013

(54) AUTOMATIC ANALYZER

(75) Inventor: Takehiko Onuma, Shioya-gun (JP)

(73) Assignee: Kabushiki Kaisha Toshiba, Kawasaki-shi (JP)

( * ) Notice: Subject to any disclaimer, the term of this patent is extended or adjusted under 35 U.S.C. 154(b) by 637 days.

(21) Appl. No.: 11/257,152

(22) Filed: Oct. 25, 2005

(65) Prior Publication Data

US 2006/0039824 A1 Feb. 23, 2006

Related U.S. Application Data

(62) Division of application No. 09/563,498, filed on May 3, 2000, now Pat. No. 7,097,808.

(30) Foreign Application Priority Data

May 7, 1999 (JP) ................................. 11-127374

(51) Int. Cl.
*B01L 3/00* (2006.01)

(52) U.S. Cl.
USPC ............ 422/68.1; 422/500; 422/501; 222/52; 137/2; 137/3; 137/4; 137/5; 137/6; 137/7; 73/1.73; 73/1.74

(58) Field of Classification Search
USPC ............ 422/68.1, 99, 100, 500, 501; 222/52; 137/2–7; 73/1.73, 1.74
See application file for complete search history.

(56) References Cited

U.S. PATENT DOCUMENTS

| 4,475,666 A | 10/1984 | Bilbrey et al. |
| 4,821,586 A | 4/1989 | Scordato et al. |
| 4,905,526 A | 3/1990 | Magnussen et al. |
| 5,228,485 A | 7/1993 | Lewis et al. |
| 5,397,539 A * | 3/1995 | Hayashi et al. ................. 422/65 |
| 5,494,801 A | 2/1996 | Bogart et al. |
| 5,670,113 A | 9/1997 | Akong et al. |
| 5,687,092 A * | 11/1997 | Bretmersky et al. .......... 702/100 |
| 6,090,348 A | 7/2000 | Steele et al. |
| 6,625,546 B2 | 9/2003 | Sepetov et al. |
| 2002/0031446 A1 | 3/2002 | Friedlander et al. |
| 2003/0207464 A1 | 11/2003 | Lemmo et al. |

FOREIGN PATENT DOCUMENTS

| JP | 60-176158 | 11/1985 |
| JP | 02087069 A | 3/1990 |
| JP | 3-9263 | 1/1991 |
| JP | 3-82965 | 4/1991 |
| JP | 4-71170 | 6/1992 |
| JP | 4-291159 | 10/1992 |
| JP | 4-329364 | 11/1992 |
| JP | 5-252993 | 10/1993 |
| JP | 8-146009 | 6/1996 |
| JP | 2000-321288 | 11/2000 |

* cited by examiner

*Primary Examiner* — Brian R Gordon
*Assistant Examiner* — Shogo Sasaki
(74) *Attorney, Agent, or Firm* — Oblon, Spivak, McClelland, Maier & Neustadt, L.L.P.

(57) ABSTRACT

An automatic analyzer analyzes a measurement item by making a sample and reagent react with each other and measuring the reaction result. This apparatus allows parameters associated with reagent dispensing executed by a reagent dispensing mechanism to be set as a dispensing condition for each measurement item or each type of reagent, and controls the reagent dispensing mechanism on the basis of the dispensing condition.

13 Claims, 6 Drawing Sheets

| REAGENT | ASPIRATION SPEED | DISCHARGE SPEED | AIR GAP AMOUMT | DUMMY AMOUNT |
|---|---|---|---|---|
| REAGENT A | CONDITION 1 | CONDITION 1 | 20 μℓ | 10 μℓ |
| REAGENT B | CONDITION 1 | CONDITION 2 | 20 μℓ | 10 μℓ |
| REAGENT C | CONDITION 2 | MANUAL CONDITION 2 | 30 μℓ | 10 μℓ |

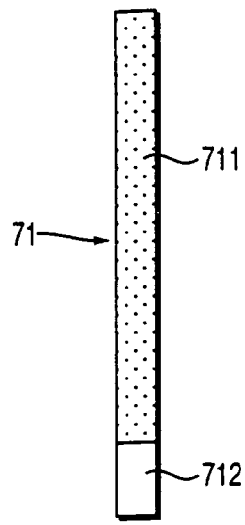
F I G. 2A
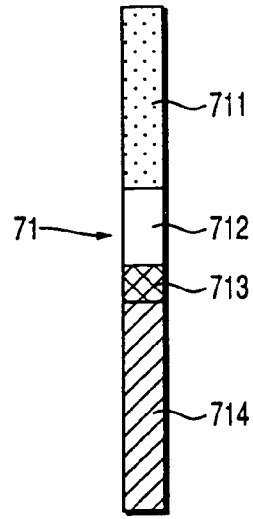
F I G. 2B
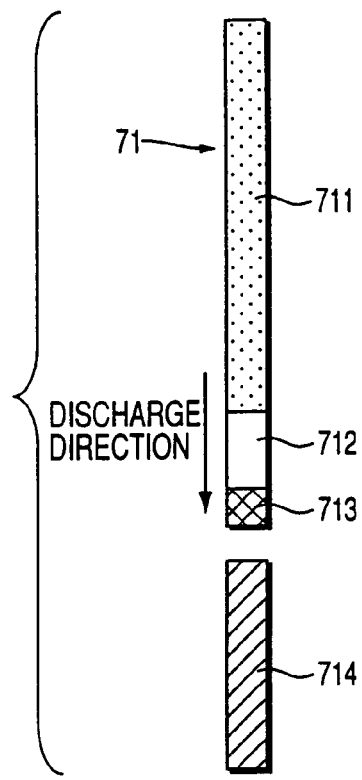
F I G. 2C
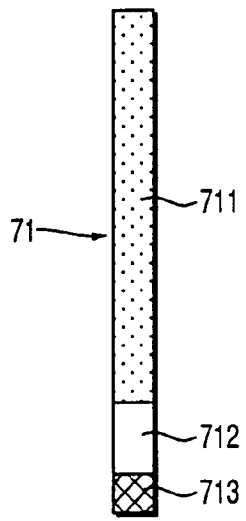
F I G. 2D
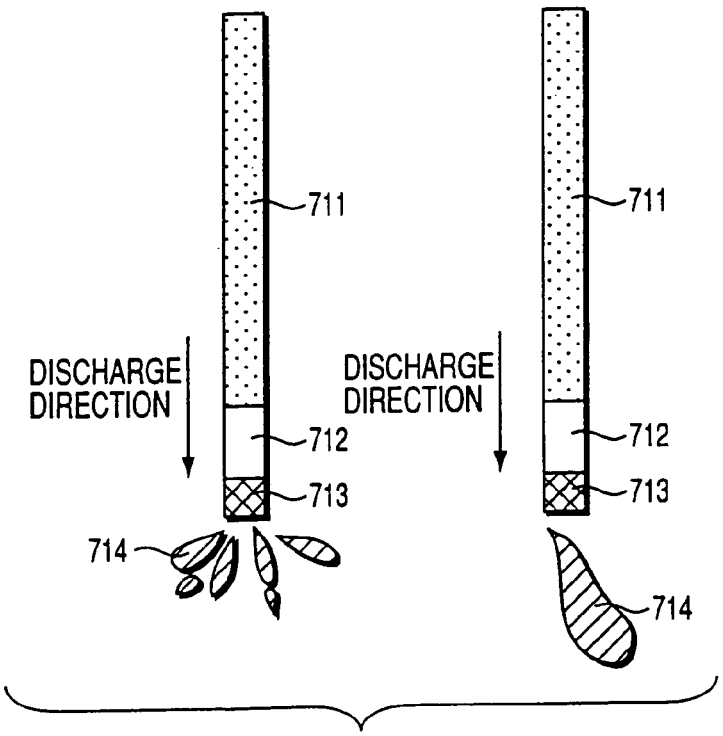
F I G. 3

| DISPENSING CONDITION | CHARACTERISTICS |
|---|---|
| [DEFAULT] | CONDITION IN WHICH FOUR PARAMETERS ARE SET TO VALUES USED BY CONVENTIONAL AUTOMATIC ANALYZER |
| [TYPE-1] | CONDITION IN WHICH FOUR PARAMETERS ARE SET TO VALUES AIMING AT REDUCING REAGENT DIMMY AMOUNT |
| [TYPE-2] | CONDITION IN WHICH FOUR PARAMETERS ARE SET TO VALUES AIMING AT ENHANCING AGITATING EFFECT |
| [TYPE-3] | CONDITION IN WHICH FOUR PARAMETERS ARE SET TO VALUES AIMING AT SUPPRESSING FOAMING |
| [TYPE-4] | CONDITION IN WHICH FOUR PARAMETERS ARE SET TO VALUES CORRESPONDING TO REAGENT WITH HIGH VISCOSITY, IN PARTICULAR |
| [TYPE-5] | CONDITION IN WHICH FOUR PARAMETERS ARE SET TO VALUES CORRESPONDING TO REAGENT WITH HIGH SPECIFIC GRAVITY, IN PARTICULAR |

FIG. 4

| MEASUREMENT ITEM | DISPENSING CONDITION |
|---|---|
| ITEM A (REAGENT A) | DEFAULT |
| ITEM B (REAGENT B) | TYPE-1 |
| ITEM C (REAGENT C) | TYPE-2 |
| ITEM D (REAGENT D) | TYPE-3 |
| ITEM E (REAGENT E) | TYPE-4 |
| ITEM F (REAGENT F) | TYPE-5 |

FIG. 5

|  | ASPIRATION SPEED | DISCHARGE SPEED |
|---|---|---|
| ITEM A (REAGENT A) | CONDITION 1 | CONDITION 1 |
| ITEM B (REAGENT B) | CONDITION 1 | CONDITION 2 |
| ITEM C (REAGENT C) | CONDITION 2 | CONDITION 1 |

FIG. 6A

|  | ASPIRATION SPEED | DISCHARGE SPEED |
|---|---|---|
| ITEM A (REAGENT A) | CONDITION 1 | CONDITION 1 |
| ITEM B (REAGENT B) | MANUAL CONDITION 1 | CONDITION 2 |
| ITEM C (REAGENT C) | CONDITION 2 | CONDITION 1 |

FIG. 6B

|  | ASPIRATION SPEED | DISCHARGE SPEED |
|---|---|---|
| ITEM A (REAGENT A) | CONDITION 1 | CONDITION 1 |
| ITEM B (REAGENT B) | MANUAL CONDITION 1 | CONDITION 2 |
| ITEM C (REAGENT C) | CONDITION 2 | FULL MANUAL CONDITION 2 |

FIG. 6C

| REAGENT | ASPIRATION SPEED | DISCHARGE SPEED | AIR GAP AMOUMT | DUMMY AMOUNT |
|---|---|---|---|---|
| REAGENT A | CONDITION 1 | CONDITION 1 | 20 μℓ | 10 μℓ |
| REAGENT B | CONDITION 1 | CONDITION 2 | 20 μℓ | 10 μℓ |
| REAGENT C | CONDITION 2 | MANUAL CONDITION 2 | 30 μℓ | 10 μℓ |

FIG. 8A

| REAGENT | DISCHARGE SPEED | DUMMY AMOUNT |
|---|---|---|
| REAGENT A | CONDITION 1 | 10 μℓ |
| REAGENT B | CONDITION 2 | 10 μℓ |
| REAGENT C | CONDITION 1 | 10 μℓ |

FIG. 8B

AUTOMATIC ANALYZER

CROSS-REFERENCE TO RELATED APPLICATIONS

This application is a divisional of U.S. application Ser. No. 09/563,498 filed May 3, 2000, now U.S. Pat. No. 7,097,808 and further is based upon and claims the benefit of priority from the Japanese Patent Application No. 11-127374, filed May 7, 1999, the entire contents of each of which are incorporated herein by reference.

BACKGROUND OF THE INVENTION

The present invention relates to a sample analyzer having a dispensing mechanism for dispensing a reagent or the like.

An automatic analyzer is an apparatus designed to automatize a procedure for mixing a reagent into a sample (specimen), e.g., a bodily fluid such as blood, urine, or cerebrospinal fluid or tissue and performing component analysis and inspection by checking reactions by light. Analysis and inspection can be done in large quantities at once by using this automatic analyzer. Such apparatuses are therefore widely used in hospitals, testing laboratories, and the like, greatly contributing to an improvement in operability.

FIG. 1 shows a general automatic analyzer. General automatic analysis processing will be described below with reference to FIG. 1.

First of all, a sampler 2 rotates by a predetermined amount to move a sample vessel 201 containing a sample as an analysis/measurement target to the position of a sample dispensing mechanism 3. The sample dispensing mechanism 3 aspirates the sample through a probe 31, and discharges the sample in an amount required for analysis processing (required amount) into a reaction vessel 41. Thereafter, a reaction unit 4 further rotates and stops at the position of a reagent dispensing mechanism 7 or 8. The reagent dispensing mechanism 7 or 8 aspirates a reagent used for a measurement item of the sample in the reaction vessel 41 from a reagent reservoir 5 or 6 through a probe 71 or 81, and discharges the required amount of reagent into the reaction vessel 41, thereby executing reagent dispensing. The reaction vessel 41 then moves to the position of an agitating unit 9, so that the mixture of the sample and reagent in the reaction vessel 41 is agitated by an agitating rod 91 of the agitating unit 9. The reaction vessel 41 is analyzed by, for example, a photometer (not shown). After the analysis, the reaction vessel 41 is cleaned by a cleaning mechanism 11 and used for the next sample analysis.

FIGS. 2A, 2B, 2C and 2D are views for explaining one cycle of dispensing operation by the sample dispensing mechanism 3, 7, or 8 shown in FIG. 1. Although FIGS. 2A, 2B, 2C and 2D show a cross-section of the probe 71 of the reagent dispensing mechanism 7 as an example, its arrangement and operation are the same as those of the sample dispensing mechanism 3 or 8.

Dispensing executed by the reagent dispensing mechanism 7 will be described next.

FIG. 2A is a sectional view of the probe 71 before the aspiration of the reagent. FIG. 2B is a sectional view of the probe 71 after the aspiration of the reagent. FIGS. 2C and 2D are sectional view of the probe 71 after the discharge of the reagent.

Referring to FIG. 2A, the probe 71 before the aspiration of the reagent is filled with water 711 that is aspirated in advance. The reagent dispensing mechanism 7 moves up and down and rotates to insert the probe 71 into a reagent vessel 51, and aspirates a predetermined amount of reagent at a predetermined aspiration speed, as shown in FIG. 2B. In FIG. 2B, a measurement reagent 714 is a reagent that is discharged into the reaction unit 4 in an amount required for measurement. An air gap 712 is an air layer that is aspirated before the aspiration of the reagent to prevent the mixing of the reagent with the water. The reagent aspirated as shown in FIG. 2B is discharged as shown in FIG. 2C to be set in the state shown in FIG. 2D. Thereafter, the inside of the probe 71 is cleaned with water 111, and one cycle of reagent dispensing is completed.

In general, when a reagent is aspirated in dispensing, an excess amount 713 of reagent is aspirated as shown in FIG. 2B, in addition to the amount of reagent required for measurement. This operation is performed to compensate for a decrease in reagent concentration due to the mixing of the reagent with the water left on the inner wall of the probe 71.

This reagent aspirated in an excess amount will be referred to as "reagent dummy" hereinafter. In general, the amount of reagent dummy 713 is determined as, for example, <discharge amount×8%+6 μl> in accordance with the amount of reagent discharged. This mathematical expression is applied regardless of the measurement item (the type of reagent). Note that the measurement reagent 714 and reagent dummy 713 are the same, but are illustrated distinct from each other in FIGS. 2A to 2D for the sake of descriptive convenience.

Recently, as a method of decreasing the running cost of the automatic analyzer 1, an attempt has been made to decrease the amount of reagent dummy. In this case, according to a conventional automatic analyzer, the amount of reagent dummy is uniformly decreased from, for example, <discharge amount×8%+6 μl> to <discharge amount×4%+3 μl> regardless of the analysis item or the type of reagent.

Depending on the measurement item (reagent), however, the reagent may scatter or drip from the distal end of the probe 17 when the reagent is discharged, as shown in FIG. 3. This inconvenience occurs because when the amount of reagent dummy is changed, the density and the like vary, and the physical condition for proper dispensing falls outside an allowable range.

Reagents have different components and properties (e.g., surface active effect, viscosity, foaming, and the like). For example, even at the same discharge speed, reagents are basically discharged from the probe in different states depending on their types. Even at a discharge speed at which a given reagent does not foam, another reagent may scatter or drip when they are discharged, or agitation of another reagent and a sample may become insufficient in dispensing operation. As described above, therefore, if the amount of reagent dummy is decreased uniformly regardless of the analysis item or type of reagent, the occurrence of such an inconvenience seems inevitable.

According to the conventional automatic analyzer, factors (e.g., the amount of reagent dummy described above) that determine the physical condition of a reagent in dispensing cannot be defined for each analysis item or each type of reagent. This leads to a low degree of freedom in terms of the use of the apparatus and low compatibility with respect to reagents, as typically indicated by the above reduction in reagent dummy amount.

BRIEF SUMMARY OF THE INVENTION

The present invention has been made to solve the above problem, and has as its object to provide an automatic analyzer which allows factors that define the physical condition of a reagent in dispensing to be defined for each analysis item or each type of reagent, exhibits a high degree of freedom in terms of the use of the apparatus, and more specifically, dispensing, and is compatible to any kind of reagent.

The present invention according to the first aspect is an automatic analyzer for analyzing a measurement item by making a sample and a reagent react with each other and measuring a reaction result which comprises: reagent dispensing means for executing a dispensing operation wherein the reagent dispensing means aspirates the reagent from a reagent vessel and discharges the reagent into a reaction vessel; and control means for controlling the dispensing operation for each measurement item or each reagent on the basis of a parameter associated with dispensing of the reagent.

The present invention according to the second aspect is an analyzer according to the first aspect wherein the parameter includes at least one of an aspiration speed of the reagent a discharge speed of the reagent, an air gap amount, and a reagent dummy amount in the dispensing operation by the reagent dispensing means.

The present invention according to the third aspect is an apparatus according to the second aspect wherein the apparatus further comprises setting means for setting the parameter and the control means controls the dispensing operation for each measurement item or each reagent on the basis of the parameter set by the setting means.

The present invention according to the fourth aspect, an apparatus according to the second aspect wherein the apparatus further comprises storage means for storing the plurality of predetermined parameters and the control means controls the dispensing operation for each measurement item or each reagent on the basis of the parameter selected from the storage means by an operator.

The present invention according to the fifth aspect of, an apparatus according to the second aspect wherein each of the aspiration and discharge speed is determined by an initial speed, a maximum speed, a final speed of the dispensing a time interval between the initial speed and the maximum speed, and a time interval between the maximum speed and the final speed in the dispensing operation by the reagent dispensing means.

The present invention according to the sixth aspect, an apparatus according to the second aspect wherein the control means controls the dispensing operation on the basis of a dispensing condition constituted by a combination of predetermined values of the respective parameters which are set for each measurement item or each reagent.

The present invention according to the seventh aspect is an automatic analyzer control method of analyzing a measurement item by making a sample and a reagent react with each other and measuring a reaction result which comprises the steps of: executing a dispensing operation wherein the reagent dispensing means aspirates the reagent from a reagent vessel and discharges the reagent into a reaction vessel; and controlling the dispensing operation for each measurement item or each reagent on the basis of a parameter associated with dispensing of the reagent.

The present invention according to the eighth aspect is an automatic analyzer control method according to seventh aspect wherein the parameter includes at least one of an aspiration speed of the reagent, a discharge speed of the reagent, an air gap amount, and a reagent dummy amount in the dispensing operation by the reagent dispensing means.

The present invention according to the ninth aspect is an automatic analyzer control method according to the eighth aspect wherein the control method further comprises the step of setting the parameter and the controlling step controls the dispensing operation for each measurement item or each reagent on the basis of the parameter set by the setting means.

The present invention according to the tenth aspect is an automatic analyzer control method according to the eighth aspect wherein the controlling step controls the dispensing operation for each measurement item or each reagent on the basis of a parameter set which is selected from the plurality of predetermined parameters.

The present invention according to the eleventh aspect is an automatic analyzer control method according to the eighth aspect wherein each of the aspiration and discharge speed is determined by an initial speed, a maximum speed, a final speed of the dispensing, a time interval between the initial speed and the maximum speed, and a time interval between the maximum speed and the final speed in the dispensing operation by the reagent dispensing means.

The present invention according to the twelfth aspect is an automatic analyzer control method according to the eighth aspect wherein the controlling step controls the dispensing operation on the basis of a dispensing condition constituted by a combination of predetermined values of the respective parameters which are set for each measurement item or each reagent.

According to any one of the aspects described above, an automatic analyzer which exhibits a high degree of freedom in terms of dispensing and is compatible to any kind of reagent can be implemented.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 2A, 2B, 2C, and 2D are views for explaining one cycle of dispensing operation by the sample dispensing mechanism 3, 7, or 8 shown in FIG. 1;

FIG. 3 is a view for explaining the dispensing operation of the sample dispensing mechanism 3, 7, or 8 shown in FIG. 1;

FIG. 4 is a view showing a dispensing condition table indicating the dispensing conditions defined by four parameters;

FIG. 5 is a view showing a setting window for setting a dispensing condition for each analysis item or each type of reagent;

FIGS. 6A, 6B, and 6C are views showing setting windows for manually setting the respective dispensing parameters;

FIGS. 8A and 8B are views showing setting windows for manually setting the respective dispensing parameters.

DETAILED DESCRIPTION OF THE INVENTION

Figure 1:
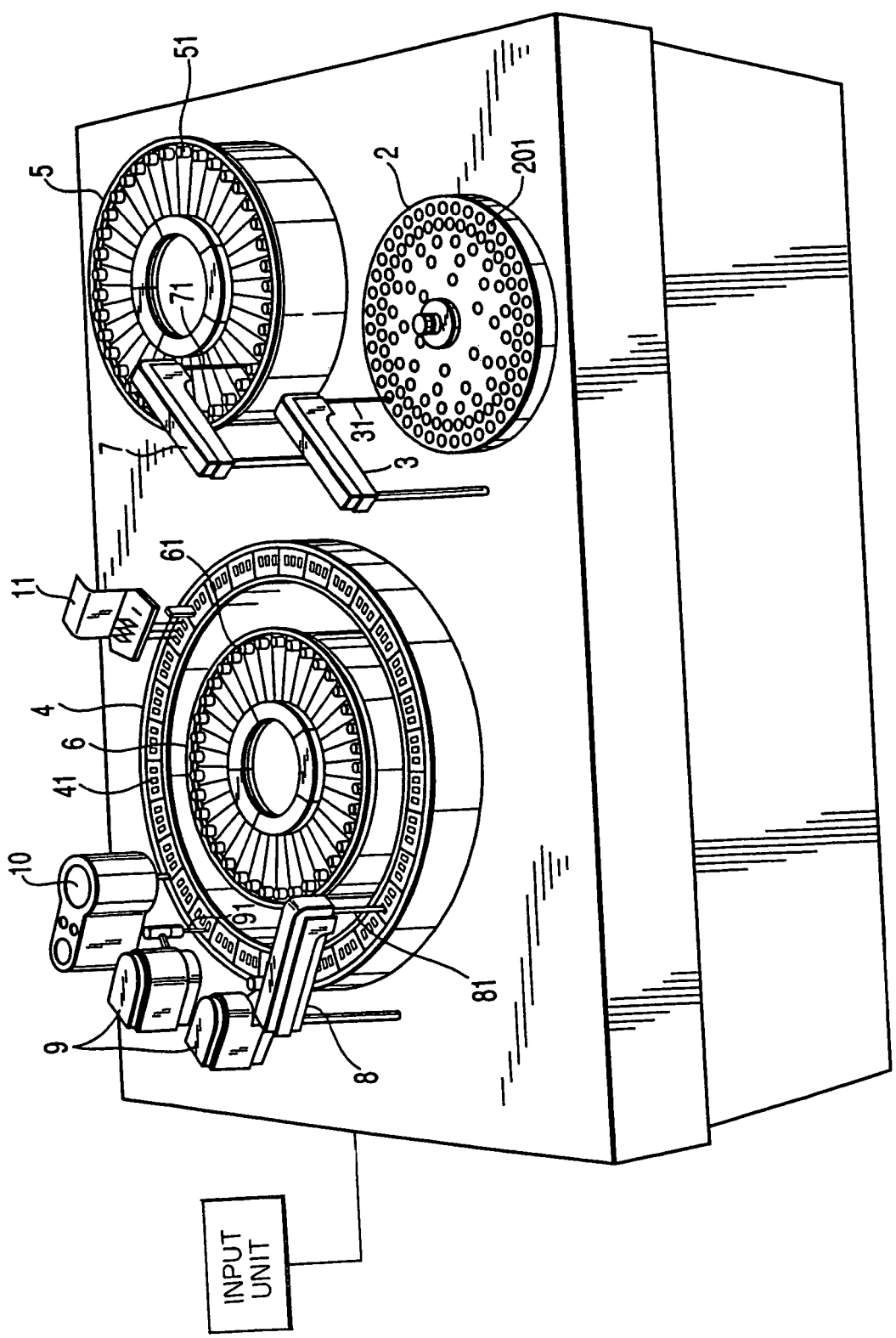
FIG. 1 is a perspective view of an automatic analyzer.

An embodiment of the present invention will be described below with reference to the views of the accompanying drawing. In the following description, the same reference numerals denote constituent elements having substantially the same functions and arrangements, and a repetitive description will be made only when required.

FIG. 1 is a perspective view of an automatic analyzer according to the present invention.

The arrangement of an automatic analyzer 1 according to the present invention will be described in brief first with reference to FIG. 1.

Referring to FIG. 1, the automatic analyzer 1 is comprised of a sample dispensing mechanism 3, reagent dispensing mechanisms 7 and 8, an agitating unit 9 for agitating the mixture of a sample and a reagent, a reaction unit 4 in which reaction vessels 41, each used for the reaction of a sample and a reagent, are disposed, a cleaning mechanism 11, a sampler 2 in which sample vessels 201 for containing samples are disposed, and reagent reservoirs 5 and 6 in which reagent vessels 51 and 61 containing various reagents are disposed.

Automatic analysis processing including reagent dispensing executed by the automatic analyzer 1 will be described first.

Referring to FIG. 1, the sampler 2 rotates by a predetermined amount to move the sample vessel 201 (e.g., a test tube) containing a sample as an analysis/measurement target to the position of the sample dispensing mechanism 3. The sample in the sample vessel 201 mounted in the sampler 2 is aspirated by the sample dispensing mechanism 3 having a probe 31 by a predetermined amount and discharged into a plurality of reaction tubes 4 made of hard glass or the like.

Subsequently, the reaction unit 4 further rotates and stops at the position of the reagent dispensing mechanism 7 or 8. The reagent dispensing mechanisms 7 and 8 rotate and move up and down to insert probes 71 and 81 into the reagent vessels 51 and 61. In accordance with the contents described later, the reagent dispensing mechanisms 7 or 8 aspirates a reagent used for a measurement item of the sample in the reaction vessel 41 from the reagent reservoir 5 or 6 through the probe 71 or 81, and discharges the reagent into the reaction vessel 41 in a required amount, thus dispensing the reagent. Note that the aspiration and discharge through the prove 71 or the like are executed by a pump (not shown).

After the reagent is dispensed into the reaction unit 4, the reaction vessel 41 moves to the position of the agitating unit 9. The sample and reagent in the reaction unit 4 are then agitated and mixed by the agitating unit 9 having an agitating member.

After the agitating/mixing operation, the absorbance of the sample in the reaction vessel 41 is measured by a photometric unit (not shown), thereby analyzing a specific component of the sample. In addition, a specific electrolyte is measured by an electrolyte measuring unit 10, as needed.

After the above specific component analysis or electrolyte measurement, the reaction unit 4 is cleaned by the cleaning mechanism 11.

Each sample set in the sampler 2 is repeatedly analyzed by such a series of operations.

Reagent dispensing operation executed by the automatic analyzer 1 will be described next. The dispensing operation is a series operation for aspirating the reagent from the reagent vessel 51, 61 and discharging the reagent into the reaction vessel 41. Control on this dispensing is a specially important point of the present invention and will be described below. Assume that four factors that determine the physical condition of a reagent in dispensing are regarded as parameters (to be referred to as dispensing parameters hereinafter) associated with reagent dispensing operation. As these dispensing parameters, unique values are set for each analysis item or each type of reagent, and dispensing operation is executed on the basis of the set values of the dispensing parameters.

Note that control associated with this dispensing operation is executed by a control unit (not shown). In the following description, the reagent dispensing mechanism 7 will be exemplified. However, the same control can be applied to each reagent dispensing mechanism.

Dispensing parameters will be described below. As parameters associated with dispensing operation (i.e., dispensing parameters), the following four parameters are conceivable: "aspiration speed", "discharge speed", "air gap amount", and "dummy amount".

"Aspiration speed" indicates the dispensing speed of a reagent when the reagent dispensing mechanism 7 aspirates the reagent from the reagent vessel 51 through the probe 71. "Discharge speed" indicates the dispensing speed of a reagent when the reagent dispensing mechanism 7 discharges the reagent into the reaction vessel 41 through the probe 71. "Air gap amount" indicates the volume of a space produced between a water portion and a reagent portion when the reagent dispensing mechanism 7 aspirates water through 71 first, and then aspirates air before the aspiration of the reagent so as to prevent the mixing of the reagent with the water. "Dummy amount" indicates the volume of a reagent dummy aspirated from the reagent vessel 51 by the reagent dispensing mechanism 7 through the probe 71.

At least one of these four parameters is associated with the occurrence of scattering, dripping, or foaming of a reagent, a discharge amount error, or the like which affects measurement in reagent dispensing. For example, "air gap amount" is a parameter that affects the amount of reagent discharged. An error may occur in the amount of reagent discharged owing to the pressure difference between the reagent and the air gap in draining the reagent from the probe.

FIG. 4 shows a dispensing condition table showing dispensing conditions defined by the above four parameters and the characteristics of the conditions. This dispensing condition table is stored in a storage unit (not shown) in the automatic analyzer 1.

The dispensing conditions are defined by combinations of the set values of the four parameters recommended by the apparatus in accordance with purposes. For example, "TYPE-1" aims at reducing the amount of reagent dummy and represents a dispensing condition in which the respective parameters are set as follows: "aspiration speed"=an aspiration speed or rate (ml/s) measured at a point of time that is during the period between the start and the end of aspiration (or a pumping rate [pps] at which the pump is driven at a point of time that is during the period between the start and end of aspiration), "discharge speed"=a discharge speed or rate (ml/s) measured at a point of time that is during the period between the start and the end of discharge (or a pumping rate [pps] at which the pump is driven at a point of time that is during the period between the start and end of discharge), "air gap amount"=a µl, and "dummy amount"=b %+c µl (a, b and c, are constants). The operator selects a condition applied to each measurement item (reagent) from these dispensing conditions.

FIG. 5 shows a setting window for setting a dispensing condition for each analysis item (each type of reagent).

The operator sets a dispensing condition for each analysis item (each type of reagent) through this setting window displayed on a display unit (not shown) before, for example, the start of analyzing operation. This dispensing condition setting is executed by selecting a desired condition from the above table. Each reagent is dispensed on the basis of the corresponding dispensing condition set in this manner. Note that the contents set through this window can be changed by invoking the setting window shown in FIG. 5 at an arbitrary timing when an inconvenience occurs during reagent dispensing.

The variety of dispensing operations can be increased by adding new dispensing conditions to the dispensing condition table shown in FIG. 4 by external input operation or the like. If required, the operator can manually set new dispensing conditions. This manual setting of dispensing conditions will be described in detail later.

According to this arrangement, the above four parameters can be set for each analysis item or each type of reagent. Therefore, an automatic analyzer exhibiting a high degree of freedom in uses associated with dispensing in particular can be provided.

Several examples of dispensing implemented by the automatic analyzer having the above arrangement will be described below.

EXAMPLE 1

The Amount of Reagent Dummy is to be Reduced

Assume that the amount of reagent dummy is reduced to reduce the running cost in association with item A shown in FIG. 5.

As shown in FIG. 5, in item A, "DEFAULT" is set as a dispensing condition. In this case, the operator can reduce the amount of reagent dummy as compared with the previous amount by setting dispensing condition "TYPE-1", which aims at reducing the amount of reagent dummy, as a new dispensing condition in item A. Alternatively, as described later, the operator may simply reduce only the amount of reagent dummy by manual operation.

With regard to many types of reagents, the amounts of reagent dummies can be reduced by changing the dispensing condition to "TYPE-1". In addition, proper dispensing can be performed. Depending on reagents, however, inconveniences such as foaming and dripping may occur upon making a change to dispensing condition "TYPE-1". In some case, these inconveniences can be eliminated by changing the set values of the three other parameters as well as the amount of reagent dummy.

That is, the four parameters influence the physical state of a reagent in dispensing operation as they correlate with each other in a complicated manner. Therefore, preferable dispensing (in this case, minimizing the amount of reagent dummy without causing any inconvenience such as foaming) may be implemented by manipulating the three other parameters instead of only reducing the amount of reagent dummy. It is, however, difficult to artificially manipulate these four parameters having a complicated correlation so as to perform proper dispensing. This poses a problem in terms of convenience. For these reasons, the automatic analyzer according to this embodiment uses the concept of a dispensing condition constituted by a combination of set values to perform dispensing control for each measurement item or each type of reagent in accordance with the dispensing condition.

Although not shown in FIG. 4, in the automatic analyzer according to this embodiment, a plurality of recommended dispensing conditions, other than "TYPE-1", associated with a reduction in the amount of reagent dummy are prepared. The operator may examine/inspect these recommended dispensing conditions to set an optimum dispensing condition for the purpose of reducing the amount of reagent dummy without causing any inconvenience such as foaming.

According to this arrangement, the amount of reagent dummy can be easily reduced while a proper dispensing precision is maintained. Even if an inconvenience such as foaming occurs when the amount of reagent dummy is reduced, a dispensing condition suitable for the purpose can be quickly and easily examined and set.

EXAMPLE 2

Reagent Having High Specific Gravity

In general, when a reagent is discharged onto a sample in dispensing operation, it can be expected that the reagent and sample are agitated. With a reagent having a high specific gravity, however, this agitating effect may be low. Assume that in this example, a reagent used for item B in FIG. 5 has a high specific gravity, and dispensing is performed to obtain a high agitating effect by setting a high discharge speed or the like.

As shown in FIG. 5, in item B, "TYPE-1" is set as a dispensing condition. In this case, when the operator sets dispensing condition "TYPE-2" aiming at improving the agitating effect as a new dispensing condition in item B, an agitating effect higher than that in general reagent dispensing can be obtained. Alternatively, the operator may simply increase the discharge speed by manual operation, as will be described later. As described in Example 1, however, control based on dispensing conditions is superior in operability.

Assume that an inconvenience such as foaming occurs when the dispensing condition is changed to "TYPE-2". In this case, the operator may examine/inspect a plurality of dispensing conditions (not shown in FIG. 4), other than "TYPE-2" recommended by the apparatus, aiming at improving the agitating effect so as to set an optimum dispensing condition for the purpose of reducing the amount of reagent dummy without causing any inconvenience (foaming in this case).

With this arrangement, the operator can easily improve the agitating effect while maintaining a proper dispensing precision. In addition, even if an inconvenience such as foaming occurs in a predetermined dispensing condition, a dispensing condition suitable for the purpose can be quickly and easily examined/set.

EXAMPLE 3

Others

In other cases wherein, for example, dripping occurs, which is likely to be caused in a reagent having a high viscosity, and scattering occurs because of improper parameter values, such inconveniences can be properly handled by examination/inspection performed in the same manner as described above.

EXAMPLE 4

New Reagent

An example of how dispensing conditions are set for new reagents will be described next.

Recently, new reagents have been developed one after another. Conventional automatic analyzers may not be suited for these reagents. This is because these analyzers cannot perform control based on dispensing parameters for each measurement item (each type of reagent), and have low compatibility with reagents.

In contrast to this, the automatic analyzer according to this embodiment can properly dispense even a new reagent by the following procedure. A new reagent will be referred to as a reagent X hereinafter.

First of all, for example, dispensing condition "DEFAULT" is set, and dispensing is executed. If no inconvenience occurs in dispensing in this dispensing condition, an attempt may be made to reduce the amount of reagent dummy so as to reduce the running cost. The amount of reagent dummy is reduced by the same procedure as described above.

If an inconvenience such as foaming, dripping, or scattering occurs in dispensing in dispensing condition "DEFAULT", each inconvenience is handled by a corresponding measure. This handling method has also been described above.

In this manner, dispensing is experimentally executed in, for example, dispensing condition "DEFAULT", and proper dispensing conditions are inspected/examined in accordance with purposes thereafter, thereby properly dispensing even new reagents.

According to this arrangement, therefore, even if a new reagent is introduced, an optimum dispensing condition can be quickly and easily examined/set for the reagent.

EXAMPLE 5

Manual Operation

Manual setting of dispensing parameters will be described next.

As described in Examples 1 to 4, the automatic analyzer according to this embodiment basically performs control on dispensing by selecting/setting a dispensing condition stored in advance for each measurement item (each type of reagent). In some case, however, the operator may want to manually set dispensing parameters.

The automatic analyzer according to this embodiment can execute dispensing control based on manual setting by the operator, thus further increasing the degree of freedom in dispensing.

Three methods of setting two dispensing parameters, i.e., the aspiration speed and discharge speed of a reagent, will be described first.

FIGS. 6A, 6B, and 6C respectively show setting windows for setting aspiration speeds and discharge speeds based on the probe 71 for the respective measurement items (the respective types of reagents). These windows are displayed on the display unit (not shown).

First, an example of setting an aspiration speed and discharge speed by the first method will be described next.

FIG. 6A shows a setting window for setting an aspiration speed and discharge speed by the first method.

Figure 7A:
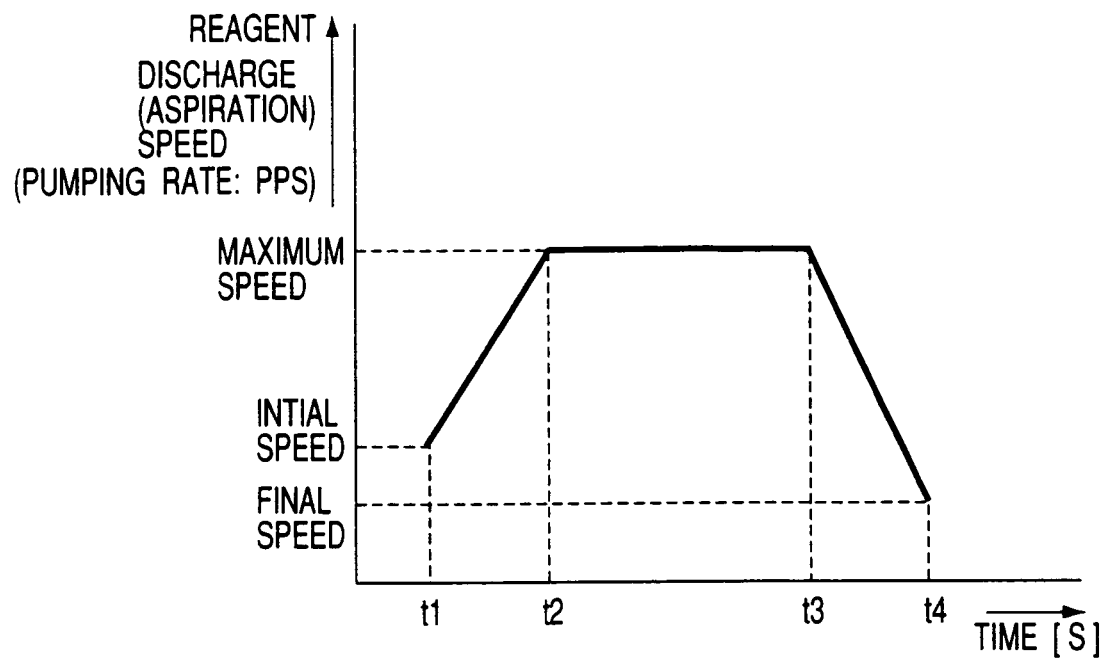
FIG. 7A is a graph showing the relationship between the speed and time in "condition 1"

The operator sets the aspiration and discharge speeds of a reagent through the setting window in FIG. 6A before, for example, dispensing operation. The operator sets these aspiration and discharge speeds by arbitrarily selecting them from a plurality of speed conditions classified into condition 1 to condition n in advance. Each speed condition is a reagent speed pattern that is set by the initial speed, maximum speed, and final speed at which the reagent dispensing mechanism 7 aspirates or discharge a reagent, the time interval between the initial speed and the maximum speed or the time interval between the maximum speed and the final speed, and the like. For example, FIG. 7A shows the relationship between the time and the dispensing speed of a reagent in "condition 1".

As described above, an aspiration speed and discharge speed are set by selecting them from n speed conditions predetermined by setting speed changes in steps. This arrangement is employed in consideration of the convenience to the operator. With this arrangement, therefore, an automatic analyzer exhibiting high operability and a high degree of freedom in dispensing can be provided.

An example of setting an aspiration speed and discharge speed by the second method will be described next. The second method is a method of creating and setting an arbitrary speed pattern by arbitrarily changing a desired part, e.g., the initial speed or maximum speed, on the basis of condition i (i is one of n conditions 1 to n) of speed conditions instead of selecting and setting an aspiration speed and discharge speed from speed conditions.

Assume that a new speed pattern based on condition 1 is to be manually set with respect to the aspiration speed of reagent B in FIG. 6A. The operator performs predetermined operation in the setting window in FIG. 6A to display the speed pattern graph (shown in FIG. 7A) defined by condition 1 on the display unit. The operator then creates a new "manual condition 1" by changing a desire part of the displayed speed pattern in FIG. 7A with an input unit (keyboard or mouse) as shown in FIG. 1.

Figure 7B:
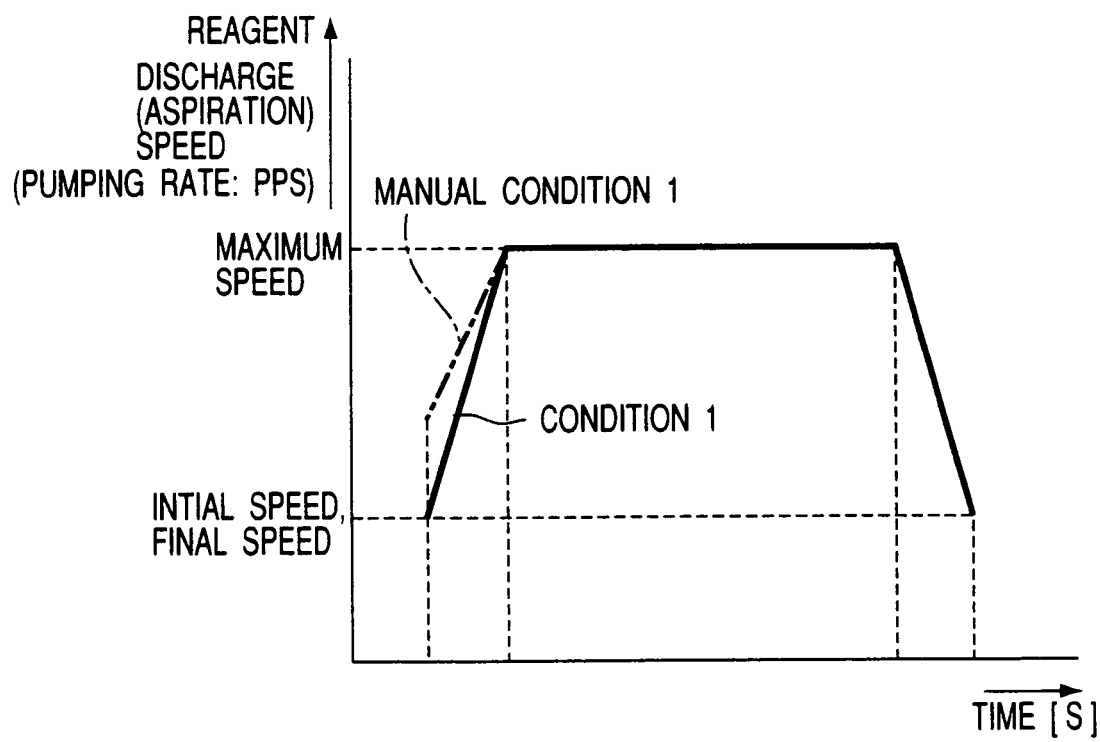
FIG. 7B is a graph showing the relationship between the speed and time in "manual condition 1"

FIG. 7B shows the speed pattern of "manual condition 1" created by changing only the initial speed of the speed pattern defined by condition 1 in FIG. 7A.

The operator may set "manual condition 1" created in this manner as an aspiration speed as shown in FIG. 6B.

As described above, in the second method, an aspiration speed and discharge speed are set on the basis of the speed pattern defined by a predetermined speed condition. This arrangement is employed in consideration of the convenience to the operator. According to this arrangement, therefore, an automatic analyzer exhibiting high operability and a high degree of freedom in dispensing can be provided.

An example of setting an aspiration speed and discharge speed by the third method will be described next. In the third method, all changes in reagent dispensing speed over time (i.e., the initial speed, maximum speed, final speed, the time interval between the initial speed and the maximum speed or the time interval between the maximum speed and the final speed, and the like) are manually set to arbitrary values without being based on any speed condition. Manual setting by the third method will be referred to as "full manual setting", and the speed condition by the full manual setting will be referred to as "full manual condition" hereinafter.

Assume that a discharge speed is set for reagent C in FIG. 6A by full manual setting. The operator can define a full manual condition by directly setting numerical values upon predetermined operation or creating a graph like the one shown in FIG. 7A. The operator may set this condition as "full manual condition", as shown in FIG. 6C. Note that "2" added to "full manual condition" is a suffix for discriminating a plurality of full manual conditions from each other.

As described above, in the third method, an aspiration speed and discharge speed are set by full manual setting. This arrangement is employed to provide an automatic analyzer having a higher degree of freedom in dispensing.

Note that "air gap amount" and "reagent dummy amount" can also be set by selecting values from predetermined values as in the first setting method. Alternatively, these values may be set by directly inputting numerical values using the third method.

An example of dispensing by a manual setting method will be described next.

Assume that measurement items for a sample as a measurement target contained in the reaction vessel 41 are items A, B, and C (or reagents A, B, and C used for measurement), as shown in FIG. 6A. In this case, the operator sets speed conditions of "aspiration speed" and "discharge speed" for the respective items (or reagents) by selecting them from "condition 1" to "condition n" before the aspiration of the reagents. If, for example, the operator selects "condition 1", reagent A used for measurement item A is aspirated through the probe 71 in accordance with the speed pattern of condition 1 (see FIG. 7A). The reagent A is then discharged into the reaction vessel 41, in which the sample as the measurement target is contained, in accordance with the speed pattern of condition 1.

Assume that foaming, dripping, or scattering occurs in dispensing reagent A. In this case, with regard to "aspiration speed" and "discharge speed" of reagent A, the operator examines/inspects speed conditions in which no foaming, dripping, or scattering occurs, and sets condition i (i is one of n conditions 1 to n) shown in FIG. 7B which is set to execute optimum dispensing.

The operator can also set new "manual condition i" by arbitrarily changing a desired part, e.g., the initial speed, on the basis of condition i. Referring to FIG. 7B, an example of "manual condition i" set by changing only the initial speed of condition i is indicated by the chain line.

In addition, the operator can arbitrarily set an initial speed, maximum speed, final speed, time interval between the initial speed to the maximum speed or time interval between the maximum speed and the final speed, and the like as "full manual condition", as needed.

If foaming, dripping, or scattering occurs during dispensing of a reagent for measurement item B (reagent B) or measurement item C (reagent C), the same processing as that for reagent A may be performed.

Since a reagent aspiration or discharge state can be controlled for each measurement item (each type of reagent) in this manner, the difference in aspiration or discharge state between different types of reagents can be accurately comprehended. This makes it possible to properly dispense any types of reagents in accordance with the reagents.

Examples of methods of reducing the amount of reagent dummy to reduce the running cost on the basis of a manual setting method will be described next with reference to FIGS. 8A and 8B. FIGS. 8A and 8B show setting windows for setting the values or conditions of the respective dispensing parameters. These windows are displayed on the display unit (not shown).

The operator inputs data of the respective parameters, "aspiration speed", "discharge speed", "air gap amount", and "reagent dummy amount", through the setting window in FIG. 8A before, for example, the start of analysis processing. With regard to "aspiration speed", and "discharge speed", conditions are set by the first and second setting methods. With regard to "air gap amount" and "reagent dummy amount", numerical values are directly input and set for each measurement item (each type of reagent) by the third setting method. In this case, in order to reduce the amount of reagent dummy, 10 µl is set, which is half the general "reagent dummy amount", 20 µl.

Each reagent used for a corresponding measurement item and air are aspirated through the probe 71 and discharged into the reaction vessel 41, in which a sample as a measurement target is contained, in accordance with the dispensing parameter settings shown in FIG. 8A.

Assume that foaming, dripping, or scattering occurs when, for example, reagent A is dispensed. In this case, with regard to dispensing parameters "aspiration speed", "discharge speed", "air gap amount", and "reagent dummy amount" for reagent A, the operator examines/inspects conditions or numerical values with which no foaming, dripping, or scattering occurs. In accordance with this result, the operator sets a numerical value or condition of a parameter that needs to be changed through the setting window with an input device (e.g., a keyboard or mouse) (not shown) again. More specifically, assume that reagent A foams, drips, or scatters in dispensing operation because of an excessive reduction in the amount of reagent dummy, and no foaming or the like occurs when the amount is 12 µl or more. In this case, for example, the value of "reagent dummy amount" of reagent A in the setting window may be changed from "10 µl" to "12 µl".

Assume also that reagent C did not foam with the initially set data. In this case, since the amount reagent dummy may be further reduced, the operator may examine/inspect the limit of the reduction in reagent dummy amount. If the amount of reagent dummy can further reduced, the operator can set a corresponding amount (e.g., 8 µl).

Note that foaming and the like in dispensing may be prevented by further combining the conditions or numerical values of the respective dispensing parameters described above. In this case, the conditions or numerical values of the parameters are preferably changed to further reduce the amount of reagent dummy.

In addition, as shown in FIG. 8B, a setting window may be configured to set only "discharge speed" and "reagent dummy amount" which are dispensing parameters that influence photometry or electrolyte measurement after dispensing in particular.

As described above, since reagent dispensing can be controlled for each measurement item (or each type of reagent) on the basis of dispensing parameters such as the amount of reagent dummy, the differences in aspiration or discharge state between different types of reagents can be accurately comprehended even if the amount of reagent dummy is reduced. This makes it possible to properly dispense any types of reagents while effectively reducing the running cost.

The present invention has been described in its preferred embodiments but is not limited to them. Various changes and modifications can be made without departing from the spirit and scope of the invention, as indicated by, for example, (1) and (2) below.

(1) Setting of dispensing parameters often depends on the physical quantities of a reagent, e.g., viscosity, specific gravity, and surface active effect. The apparatus may therefore be configured to select proper dispensing conditions or several recommended dispensing conditions by inputting these physical quantities of a reagent. In this case, each physical quantity of a reagent is preferably input by reading a bar code attached to a reagent vessel by a reagent maker.

According to this arrangement, a further improvement in operability can be realized. In addition, since inconvenience is input by optical reading, human input errors can be prevented.

(2) In the above embodiment, when "speed condition" is to be set with respect to each of dispensing parameters "aspiration speed" and "discharge speed", a condition that allows the execution of proper dispensing is selected from predetermined n conditions upon examination/inspection. If, however, there are many predetermined conditions, it takes much time and labor to examine/inspect the conditions. This may lead to a deterioration in operability.

In order to efficiently perform above examination/inspection, in addition to the above arrangement, this apparatus may therefore be configured to have a search unit for searching n conditions for "speed condition" that is most similar to the contents of a condition set as "manual condition" or "full manual condition".

More specifically, assume that foaming, dripping, or scattering occurs in dispensing that is executed upon setting condition i as "speed condition". In this case, the operator arbitrarily sets manual condition i or full manual condition i in which proper dispensing can be executed according to "manual condition" or "full manual condition" without examining the n-1 remaining conditions as "speed conditions". A proper speed condition can be selected from the n conditions by making the above search unit search the n conditions for "speed condition" that is most similar to manual condition i or full manual condition i set in this manner. The operator may set the condition selected by this search as "speed condition" again.

This search unit can therefore save the trouble of examining/inspecting n conditions to set "speed condition". This makes it possible to improve the operability.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An automatic analyzer for analyzing at least a first measurement item and a second measurement item different from the first measurement item by making a sample and a reagent react with each other and measuring a reaction result, comprising:
   at least a first reaction vessel and a second reaction vessel;
   a plurality of reagent vessels which stores at least a first reagent corresponding to the first measurement item and a second reagent corresponding to the second measurement item and different from the first reagent;
   a sample dispensing unit configured to execute a dispensing operation which includes an aspiration of a sample and a discharge of a portion of the aspirated sample into the reaction vessels;
   a reagent dispensing unit configured to execute dispensing operations which include a first aspiration of the first reagent from one of the plurality of reagent vessels, a second aspiration of a second reagent from the other of the plurality of reagent vessels, a first discharge of a portion of the aspirated first reagent into the first reaction vessel and a second discharge of a portion of the aspirated second reagent into the second reaction vessel;
   a setting unit configured to set at least first and second relationships, the first relationship being between a first dummy amount at the first aspiration and the first measurement item, the second relationship being between a second dummy amount at the second aspiration and the second measurement item, the first dummy amount being an excess amount in addition to an amount of the first reagent required for the first measurement item and the second dummy amount being an excess amount in addition to an amount of the second reagent required for the second measurement item;
   a controller configured to determine a first amount of the first aspiration of the first reagent including the first dummy amount in accordance with the first relationship and a second amount of the second aspiration of the second reagent including the second dummy amount in accordance with the second relationship, to control the reagent dispensing unit to exert the first aspiration in accordance with the first amount and exert the second aspiration in accordance with the second amount, sequentially; and
   an analyzing unit configured to measure a first reaction result of the sample and the first reagent in the first reaction vessel and a second reaction result of the sample and the second reagent in the second reaction vessel to analyze specific components of the samples in the first reaction vessel and the second reaction vessel.

2. The automatic analyzer according to claim 1, wherein the setting unit sets the first and second dummy amounts according to a condition selected from among plural predetermined conditions.

3. The automatic analyzer according to claim 1, further comprising an input through which the first and second dummy amounts are manually input.

4. The automatic analyzer according to claim 1, further comprising an input through which the first and second dummy amounts are manually selected from among plural predetermined dummy amounts.

5. The automatic analyzer according to claim 1, further comprising an input through which the first and second dummy amounts are set, by changing a coefficient within a mathematical expression indicating a relationship between the amount of the aspirated first and second reagents and the first and second dummy amounts.

6. The automatic analyzer according to claim 5, wherein the mathematical expression is $$\text{dummy amount} = (\text{the amount of aspirated reagent} \times A\,[\%] + B\,\mu l),$$

in which A and B are coefficients.

7. An automatic analyzer for analyzing at least a first measurement item and a second measurement item different from the first measurement item by making a sample and a reagent react with each other and measuring a reaction result, comprising:
   at least a first reaction vessel and a second reaction vessel;
   a plurality of reagent vessels which store at least a first reagent corresponding to the first measurement item and a second reagent corresponding to the second measurement item and different from the first reagent;
   a sample dispensing unit configured to execute a dispensing operation which includes an aspiration of a sample and a discharge of a portion of the aspirated sample into the reaction vessels;
   a reagent dispensing unit configured to execute dispensing operations which include a first aspiration of the first reagent from one of the plurality of reagent vessels, a second aspiration of a second reagent from the other of the plurality of reagent vessels, a first discharge of a portion of the aspirated first reagent into the first reaction vessel and a second discharge of a portion of the aspirated second reagent into the second reaction vessel;
   a setting unit configured to set at least first and second relationships, the first relationship being between a first dummy amount at the first aspiration and the first measurement item, the second relationship being between a second dummy amount at the second aspiration and the second measurement item, the first dummy amount being an excess amount in addition to an amount of the first reagent required for the first measurement item and the second dummy amount being an excess amount in addition to an amount of the second reagent required for the second measurement item;
   a controller configured to determine a first amount of the first aspiration of the first reagent including the first dummy amount in accordance with the first relationship and a second amount of the second aspiration of the second reagent including the second dummy amount in accordance with the second relationship, to control the reagent dispensing unit to exert the first aspiration in accordance with the first amount and exert the second aspiration in accordance with the second amount, sequentially; and an analyzing unit configured to measure a first reaction result of the sample and the first reagent in the first reaction vessel and exert the first aspiration in accordance with the first amount and the second aspiration in accordance with the second amount sequentially to analyze specific components of the samples in the first reaction vessel and the second reaction vessel.

8. The automatic analyzer according to claim 7, further comprising an input through which the first and second dummy amounts are selected from among plural predetermined conditions.

9. The automatic analyzer according to claim 7, further comprising an input through which the first and second dummy amounts are manually input.

10. The automatic analyzer according to claim 7, further comprising an input through which the first and second dummy amounts are manually selected from among plural predetermined dummy amounts.

11. The automatic analyzer according to claim 7, further comprising an input through which the first and second dummy amounts are input to be stored based on changing a coefficient within a mathematical expression indicating a relationship between the amount of the first and second aspirated reagents and the first and second dummy amounts.

12. The automatic analyzer according to claim 11, wherein the mathematical expression is the dummy amount=(the amount of aspirated reagent× $A$[%]+$B$ μl), in which A and B are coefficients.

13. An automatic analyzer for analyzing at least a first measurement item and a second measurement item different from the first measurement item comprising:

at least a first reaction vessel and a second reaction vessel;

a plurality of reagent vessels which store at least a first reagent corresponding to the first measurement item and a second reagent corresponding to the second measurement item and different from the first reagent;

a sample dispensing unit configured to execute a dispensing operation, which includes an aspiration of a sample and a discharge of a portion of the aspirated sample into the reaction vessels;

a reagent dispensing unit configured to execute dispensing operations which include a first aspiration of the first reagent from one of the plurality of reagent vessels, a second aspiration of a second reagent from the other of the plurality of reagent vessels, a first discharge of a portion of the aspirated first reagent into the first reaction vessel and a second discharge of a portion of the aspirated second reagent into the second reaction vessel;

a setting unit configured to set at least first and second relationships, the first relationship being between a first dummy amount at the first aspiration and the first measurement item the second relationship being between a second dummy amount at the second aspiration and the second measurement item, the first dummy amount being an excess amount in addition to an amount of the first reagent required for the first measurement item and the second dummy amount being an excess amount in addition to an amount of the second reagent required for the second measurement item;

a controller configured to determine a first amount of the first aspiration of the first reagent including the first dummy amount in accordance with the first relationship and a second amount of the second aspiration of the second reagent including the second dummy amount in accordance with the second relationship, to control the reagent dispensing unit to exert the first aspiration in accordance with the first amount and exert the second aspiration in accordance with the second amount, sequentially and an analyzing unit configured to measure a first reaction result of the sample and the first reagent in the first reaction vessel a second reaction result of the sample and the second reagent in the second reaction vessel, and to analyze specific components of the samples in the first reaction vessel and the second reaction vessel.

* * * * *